United States Patent [19]

Inokuchi et al.

[11] Patent Number: 5,707,649
[45] Date of Patent: Jan. 13, 1998

[54] AGENT FOR TREATING NEURONAL DISEASES

[75] Inventors: Jinichi Inokuchi, Kodaira; Seigou Usuki, Nakano-Ku, both of Japan

[73] Assignee: Seikagaku Corporation, Japan

[21] Appl. No.: 464,683

[22] PCT Filed: Aug. 12, 1994

[86] PCT No.: PCT/JP94/01342

§ 371 Date: Aug. 5, 1995

§ 102(e) Date: Aug. 5, 1995

[87] PCT Pub. No.: WO95/05177

PCT Pub. Date: Feb. 23, 1995

[30] Foreign Application Priority Data

Aug. 13, 1993 [JP] Japan ................................. 5-220518

[51] Int. Cl.$^6$ ........................ A61K 9/127; A61K 31/535
[52] U.S. Cl. ........................ 424/450; 424/459; 424/422
[58] Field of Search .......................... 424/450; 544/106, 544/89

[56] References Cited

U.S. PATENT DOCUMENTS

| | | | |
|---|---|---|---|
| 4,963,297 | 10/1990 | Madden | 264/4.3 |
| 5,041,441 | 8/1991 | Radin et al. | 514/237.8 |

OTHER PUBLICATIONS

J. Neurochem, vol.56, No.6, 1991 XP 000673625 pp. 2125–2132.

J. Neurochem, vol. 34, No. 2, 1980, XP 000673677 pp. 410–416.

Neuroprotocols, vol.3, No. 2, 1993 XP 000673697 pp. 145–155.

J. Biochem, vol. 111,pp. 191–196 (1992) Improved Inhibitors of Glucosylceramide Synthase, Akira Abe, et al.

Analytical Biochemistry, vol. 204, pp. 265–272 (1992), Simultaneous Determination of Sugar Incorporation into Glycosphingolipids and Glycoproteins, Pascal Paul, et al.

Journal of Lipid Reearch, vo.– 28, 1987 pp. 565–571.

J. Biochem, 110, pp. 96–102 (1991), Uemura et al.

Journal of Cellular Physiology, pp. 573–583 (1989) Alan R. Liss, Inc.

J. Biochem, 117 pp. 7660773 (1995), Inokuchi, et al.

Biochemical and Biophysical Res. Comm. 222, 494–498 (1996).

Journal of Neurochemistry, Lippincott–Raven Publishers, Philadelphia 1996 International Society for Neurochemistry Seigou Usuki et al pp. 1821–1830.

Ashok V. Hospatankay, Ranga R. Vunnam L. Noyman S. Radin, Lipids, vol. 17 (8) 538–542 (1982).

(List continued on next page.)

*Primary Examiner*—Thurman K. Page
*Assistant Examiner*—Murthy Sikha
*Attorney, Agent, or Firm*—Bierman, Muserlian and Lucas LLP

[57] ABSTRACT

Disclosed is an agent for curing neuronal diseases caused by disorders of peripheral nervous system or central nervous system, which comprises a 2-acylaminopropanol derivative represented by the formula (I):

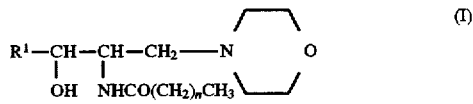

[wherein $R^1$ represents a phenyl group or cyclohexyl group each of which may be substituted by 1 to 3 same or different substituents selected from the group consisting of alkyl, alkoxy, hydroxy and nitro, or represents an alkyl group, and n represents an integer of 0 to 16] or a pharmaceutically acceptable salt thereof as an effective ingredient. It accelerates neurite extension and synapse formation by elevating biosynthesis of endogenous sphingoglycolipid of neurocytes, particularly ganglioside, whereby it can be used for curing various diseases of central nervous system and peripheral nervous system.

10 Claims, 4 Drawing Sheets

OTHER PUBLICATIONS

Jin–ichi Inokuchi & Noyman S. Radin, J. Lipid Research, 28, 565–571 (1987).

Chatterjee, Subroto et al. Glycoconjugates, J. 13(3), 481–486 (1996).
Suzzane et al. J. Cell. Physiol. 150(3), 610–19 (1992).
V.V. Ranade, J. Clin. Pharmacol. 29, 685–694 (1989).
J. Lipid Res. 32, 1991, pp. 713–722.

AGENT FOR TREATING NEURONAL DISEASES

(TECHNICAL FIELD)

This invention relates to an agent for curing neuronal diseases, which comprises a substance for accelerating biosynthesis of glycosphingolipids as an effective ingredient.

(BACKGROUND)

It has been known that glycosphingolipids (hereinafter referred to as GSL) exist as a constitutional component of cell surface membranes of mammal cells and they are closely related to a cellular function such as generation, growth, differentiation, transformation, immunoreaction, etc. through a receptor function of a physiologically active substance, an intercellular mutual recognition function, intercellular interaction, etc.

Among them, ganglioside is GSL containing sialic acid, and it is said that it has activity to recoveries from injury of peripheral nerves and a disorder of central nerves, i.e., acceleration of regeneration of nerves and a process of neurotransmission. Heretofore, effectiveness of exogenous ganglioside to various neurotic disease models has been investigated. A medicine named Cronassial$^R$ has already been put on the market in Italy as a medicine utilizing this, and a patent application pertinent thereto was filed (Japanese Provisional Patent Publication No. 34912/1977). However, there have been observed clinical cases that an anti-ganglioside antibody is generated because of administration of this medicine, i.e., the exogenous ganglioside, whereby various neurotic symptoms are caused. For example, there have been reported amyotrophic lateral sclerosis in which an anti-GM2 antibody is generated (Lancet, 337, 1109–1110, 1991) and Guillain-Barré syndrome (Lancet, 338, 757, 1991).

At present, a means for searching a function of ganglioside which has been used most frequently is a means of a type in which ganglioside is added to an experiment system from outside. In that case, a relation to endogenous ganglioside becomes a problem. That is, it is considered that a result obtained by further adding ganglioside to a system in which endogenous ganglioside existing in cell membrane has already formed a complex with various cell surface receptors, etc. does not always reflect actual cytophysiological significance of endogenous ganglioside. Thus, in order to know an inherent role of ganglioside in cytophysiology, a method of specifically changing biosynthesis of endogenous GSL is required. The present inventors have previously synthesized 1-phenyl-2-decanoylamino-3-morpholino-1-propanol (PDMP) which is an analogue of ceramide and proved that D-threo-PDMP specifically inhibits a glucosyl-ceramide biosynthesizing enzyme and extremely decreases an intracellular content of all GSL using glucosyl-ceramide as a starting substance (J. Lipid. Res., vol. 28, 565–571, 1987). Further, it has been reported that a GSL content is lowered by D-threo-PDMP, whereby extension of neurites is suppressed (J. Biochem., 110, 96–103, 1991).

On the other hand, we have found that L-threo PDMP which is an optical enantiomer of D-threo PDMP has possibility of accelerating biosynthesis of GSL (J. Cell. Physiol., 141, 573–583 (1989)). However, whether or not L-threo-PDMP increases an endogenous ganglioside level in neurocytes and whether or not increase of endogenous ganglioside activates a function of neurocytes are unknown issues and have not been investigated.

An object of the present invention is to provide an agent for curing various diseases caused by disorders of central nervous system and peripheral nervous system, using a medicine which accelerates biosynthesis of endogenous GSL in neurocytes, particularly ganglioside.

(DISCLOSURE OF THE INVENTION)

The present inventors have studied variously in order to develop an agent for curing neuronal diseases based on a new mechanism and consequently found that a specific 2-acylaminopropanol derivative accelerates biosynthesis of GSL and significantly accelerates neurite extension and synapse formation, to accomplish the present invention.

That is, the present invention is an agent for curing neuronal diseases caused by disorders of peripheral nervous system or central nervous system, which comprises a 2-acylaminopropanol derivative represented by the formula (I):

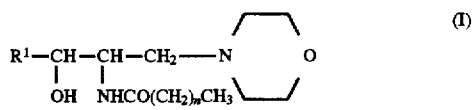

[wherein $R^1$ represents a phenyl group or cyclohexyl group each of which may be substituted by 1 to 3 same or different substituents selected from the group consisting of alkyl, alkoxy, hydroxy and nitro, or represents an alkyl group, and n represents an integer of 0 to 16] or a pharmaceutically acceptable salt thereof (hereinafter sometimes referred to as the compound of the present invention) as an effective ingredient.

Also, the present invention relates to a method of curing neuronal diseases, which comprises administering the 2-acylaminopropanol derivative represented by the above formula (I) or a pharmaceutically acceptable salt thereof in an effective amount for accelerating biosynthesis of glycosphingolipids, accelerating neurite extension and/or accelerating synapse formation to mammals which suffer from neuronal diseases caused by disorders of peripheral nervous system or central nervous system.

Also, the present invention relates to use of a medical composition which comprises the 2-acylaminopropanol derivative represented by the above formula (I), a pharmaceutically acceptable salt thereof or both of them, for preparing an agent for curing neuronal diseases caused by disorders of peripheral nervous system or central nervous system.

Further, the present invention relates to a liposome preparation composition which comprises at least the 2-acylaminopropanol derivative represented by the above formula (I) or a pharmaceutically acceptable salt thereof and a phospholipid.

In the following, the present invention is explained in detail.

In the above formula (I), the carbon number of alkyl or alkoxy as a substituent of the phenyl group or cyclohexyl group of $R^1$ is preferably 1 to 4. The carbon number of the alkyl group of $R^1$ is preferably 6 to 15, most preferably 10 to 15. The alkyl group is exemplified by hexyl, heptyl, octyl, nonyl, decyl, undecyl, dodecyl (lauryl), tridecyl, tetradecyl (myristolyl), pentadecyl, etc. n is an integer of 0 to 16, preferably an integer of 4 to 16, most preferably 6 to 12.

Among the compounds represented by the above formula (I), a particularly preferred one is 1-phenyl-2-acylamino-3-morpholino-1-propanol in which n is 6 to 12, and a most preferred one is 1-phenyl-2-decanoylamino-3-morpholino-1-propanol (hereinafter referred to as PDMP). In the compound of the present invention, stereoisomers exist, and either of the stereoisomers can be used. Also, a mixture of isomers such as a racemic mixture, etc. can be used. There may be specifically mentioned a D-threo isomer (1R, 2R), a L-threo isomer (1S, 2S), a DL-threo isomer, a D-erythro isomer (1S, 2R), a L-erythro isomer (1R, 2S) and a DL-erythro isomer. The L-threo isomer (1S, 2S) is particularly preferred from the point that it has a glycolipid piosynthesis-accelerating effect.

The compound represented by the above formula (I) is a known substance (U.S. Pat. No. 5,041,441 and Japanese Provisional Patent Publication No. 254623/1989) and can be synthesized by, for example, the following method described in J. Lipid. Res., 28, 565–571, (1987) and J. Biochem., 111, 191–196, (1992).

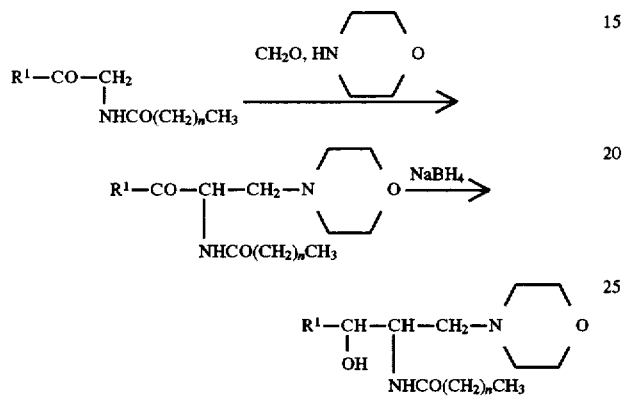

A mixture of the resulting 4 isomers can be separated by fractional crystallization using chloroform/ether to obtain a DL-threo isomer and a DL-erythro isomer, respectively. Further, the DL-threo isomer can be also crystallized as a salt of dibenzoyl-D-tartaric acid or dibenzoyl-L-tartaric acid to obtain a D-threo isomer or a L-threo isomer, respectively.

As a pharmaceutically acceptable salt of the compound represented by the above formula (I), there may be mentioned a salt of an inorganic acid such as hydrochloric acid, phosphoric acid, sulfuric acid, nitric acid, formic acid, etc.; and a salt of an organic acid such as acetic acid, citric acid, lactic acid, malic acid, oxalic acid, maleic acid, fumaric acid, succinic acid, trifluoroacetic acid, methanesulfonic acid, p-toluenesulfonic acid, etc.

By administering an effective amount of the 2-acylaminopropanol derivative represented by the formula (I) or a pharmaceutically acceptable salt thereof to mammals including human which suffer from neuronal diseases caused by disorders of peripheral nervous system or central nervous system, said animals can be treated. As a representative disease, there may be mentioned various central nervous system diseases which are expected to be cured by regenerating nerve fibers, for example apoplexy, cerebral infarction, cerebral hemorrhage, cerebral injury, dysmnesia, senile dementia, Alzheimer's disease, parkinsonism, etc.; and various peripheral nervous system diseases, for example, polyneuropathy caused by cacochymia, mechanical neuropathy, toxic neuropathy, etc.

Pharmaceutical Preparation

A pharmaceutical preparation to be administered orally or parenterally can be obtained by using the compound of the present invention with a carrier, an excipient, a diluent and other additives. Further, the compound of the present invention can pass a blood-brain barrier (J. Lipid Res., 32, 713–722 (1991)) so that effectiveness to cerebral neuronal diseases as an injection and an oral agent can be expected.

In particular, a liposome preparation having a fine size such as lipid nanosphere, etc. or a lipid emulsion preparation on which the compound of the present invention is carried can pass a blood-brain barrier by about 10 times as compared with a physiological saline solution so that it is effective when the agent of the present invention is used for curing cerebral neuronal diseases.

As an oral preparation, there may be mentioned a solid preparation such as a powder, a granule, a capsule, a tablet, etc.; and a liquid preparation such as a syrup, an elixir, an emulsion, etc.

The powder can be obtained by, for example, mixing with an excipient such as lactose, starch, crystalline cellulose, calcium lactate, calcium hydrogen phosphate, magnesium aluminometasilicate, silicic acid anhydride, etc. The granule can be obtained by adding the above excipient and, if necessary, for example, a binder such as saccharose, hydroxypropyl cellulose, polyvinylpyrrolidone, etc. or a disintegrator such as carboxymethyl cellulose, calcium carboxymethyl cellulose, etc. and granulating the mixture by a wet method or a dry method. The tablet can be obtained by tableting the above powder or granule as such or with a lubricant such as magnesium stearate, talc, etc. Further, the above tablet or granule can be made an enteric or sustained action preparation by covering it with an enteric base such as hydroxypropylmethyl cellulose phthalate, a methyl methacrylate copolymer, etc. or covering it with ethyl cellulose, carnauba wax, hardened oil, etc. A hard capsule can be obtained by filling a hard capsule with the above powder or granule. Further, a soft capsule can be obtained by dissolving the compound of the present invention in glycerin, polyethylene glycol, sesame oil, olive oil, etc. and covering the mixture with a gelatin film. The syrup can be obtained by dissolving a sweetener such as saccharose, sorbitol, glycerin, etc. and the compound represented by the above formula or a salt thereof in water. In addition to the sweetener and water, essential oil, ethanol, etc. may be added to prepare an elixir, or gum arabic, tragacanth, polysorbate 80, sodium carboxymethyl cellulose, etc. may be added to prepare an emulsion or a suspension. Further, a corrective, a coloring agent, a preservative, etc. may be added to these liquid preparations, if necessary.

As a parenteral preparation, there may be mentioned an injection, an intrarectal administration agent, a pessary, an endermic agent, an inhalant, an aerosol, an ophthalmic agent, etc.

The injection can be obtained by adding a pH-adjusting agent such as hydrochloric acid, sodium hydroxide, lactic acid, sodium lactate, sodium monohydrogen phosphate, sodium dihydrogen phosphate, etc.; an isotonizing agent such as sodium chloride, glucose, etc.; and distilled water for injection to the compound of the present invention, sterilizing and filtering the mixture and then filling an ampoule, etc. with the mixture. Further, an injection which is dissolved when it is used can be obtained by adding mannitol, dextrin, cyclodextrin, gelatin, etc. and lyophilizing the mixture under vacuum. Also, an emulsion for injection can be made by adding an emulsifier such as lecithin, polysorbate 80, polyoxyethylene hardened castor oil, etc. to the compound of the present invention and then emulsifying the mixture in water.

Further, as an injection, there may be mentioned a liposome preparation which enables improvements of solubility and a transition rate to a target organ. In particular, nanosphere liposome (lipid nanosphere) can not only heighten a concentration in blood without being taken into reticuloendothelial tissues and lower a minimum effective dose required for exhibiting a pharmaceutical effect, but also pass a blood-brain barrier easily so that it is suitable when it is used for curing cerebral neuronal diseases. The liposome preparation can be prepared according to a known liposome preparation method (C. G. Knight, Liposomes: From Physical Structure to Therapeutic Applications, pp. 51–82, Elsevier, Amsterdam, 1981; Proc. Natl. Acad. Sci., USA, 75, 4194, 1978).

That is, as an amphipathic substance forming a liposome membrane, there may be used a phospholipid such as a natural phospholipid (yolk lecithin, soybean lecithin, sphingomyelin, phosphatidylserine, phosphatidylglycerol, phosphatidylinositol, diphosphatidylglycerol, phosphatidylethanolamine, sphingomyelin, cardiolipin, etc.), a synthetic phospholipid (distearoyl phosphatidylcholine, dipalmitoyl phosphatidylcholine, dipalmitoyl phosphatidylethanolamine, etc.) and others. Further, in order to improve membrane stability, fluidity and membrane permeability of the medicine, there may be added known various additives such as cholesterols (cholesterol, ergosterol, phytosterol, sitosterol, stigmasterol, etc.), a substance which is known to impart negative charge to liposome (phosphatidic acid, dicetyl phosphate, etc.), a substance which is known to impart positive charge (stearylamine and stearylamine acetate), an antioxidant (tocopherol, etc.), an oily substance (soybean oil, cottonseed oil, sesame oil, cod-liver oil, etc.) and others.

Preparation of liposome can be carried out by, for example, the following method. The above amphipathic substance and additives, and the compound of the present invention are dissolved in an organic solvent (a single solvent such as chloroform, dichloromethane, ethanol, methanol, hexane, etc. or a mixed solvent thereof), respectively, both solutions are mixed, the organic solvent is removed in a vessel such as a flask, etc. in the presence of an inert gas (a nitrogen gas, an argon gas, etc.), and a thin membrane is attached to a vessel wall. Then, this thin membrane is added to a suitable aqueous medium (physiological saline, a buffer, a phosphate buffered physiological saline, etc.), and the mixture was stirred by a stirrer. In order to obtain liposome having a small particle size, the mixture was further dispersed by using an ultrasonic emulsifier, a pressurization type emulsifier, a French press cell pulverizer, etc. As described above, preparation of liposome proceeds by treating, with a membrane filter, a liquid in which the amphipathic substance, etc. required for preparation of liposome and the compound of the present invention are dispersed in the aqueous medium to obtain nanosphere liposome (lipid nanosphere; a particle size of about 25 to 50 nm) in which a particle size distribution is controlled. Further, liposome may be subjected to fractionation treatment such as ultrafiltration, centrifugation, gel filtration, etc. to remove the medicine which is not carried.

Further, by making the compound of the present invention to be carried on liposome having, on a membrane thereof, a glucose residue, a tyrosine residue, a mannose residue or sulfatide obtained by adding β-octylglucoside, L-tyrosin-7-amido-4-methylcoumarin, phenylaminomannoside or sulfatide as a membrane-forming substance in addition to the above amphipathic substance and additives, the liposome can be made to permeate a blood-brain barrier easily (as to a method itself, see Japanese Provisional Patent Publication No. 69332/1992).

The intrarectal administration agent can be obtained by adding a base for a suppository such as mono-, di- or triglyceride of cacao aliphatic acid, polyethylene glycol, etc. to the compound of the present invention, then melting the mixture by heating, pouring it into a mold and cooling it, or dissolving the compound of the present invention in polyethylene glycol, soybean oil, etc. and then covering the mixture with a gelatin film.

The endermic agent can be obtained by adding white petrolatum, beeswax, liquid paraffin, polyethylene glycol, etc. to the compound of the present invention, heating the mixture, if necessary, and kneading it. A tape agent can be obtained by kneading the compound of the present invention with an adhesive such as rosin, an alkyl acrylate polymer, etc. and spreading the mixture on non-woven fabric, etc. The inhalation can be obtained by, for example, dissolving or dispersing the compound of the present invention in a propellant such a pharmaceutically acceptable an inert gas, etc. and filling a pressure container with the mixture.

Administration Method

The administration method of a medicine containing the compound of the present invention as an effective ingredient is not particularly limited, but when it is used for curing neuronal diseases caused by disorders of central nervous system, an intramuscular injection, an intravenous injection, a hypodermic injection or an intraperitoneal injection is preferred. Particularly when it is used for curing cerebral hentonal diseases, a method of injecting the liposome preparation or the lipid emulsion preparation.

Dose

The dose may be suitably determined depending on administration method, age, health condition, weight, etc. of a patient, but it is generally 0.25 to 200 mg/kg, preferably 0.5 to 100 mg/kg by one dose or divided doses per day.

Acute Toxicity

A solution of L-threo-PDMP hydrochloride dissolved in a nonionic surfactant (Myrj 52) was administered intraperitoneally to ICR mice (male, 6 weeks old, weight: about 28 to 30 g). The $LD_{50}$ value was 350 mg/kg.

A solution of DL-threo-PDMP hydrochloride or DL-erythro-PDMP hydrochloride dissolved in DMSO (125 mg/ml) was administered intraperitoneally to ICR mice (male, 8 weeks old, weight: about 38 to 40 g). The $LD_{50}$ value of DL-threo-PDMP was about 250 mg/kg, and that of DL-erythro-PDMP was about 700 mg/kg.

General Toxicity

Solutions of L-threo-PDMP hydrochloride and DL-threo-PDMP hydrochloride dissolved in a nonionic surfactant (Myrj 52), respectively, were administered (intraperitoneally) at a rate of 100 mg/kg/day (calculated on the above PDMP hydrochloride) to ICR mice continuously for 10 days. As to either of the compounds, neither decrease in weight nor decrease in neutrophile, acidocyte, etc. due to suppression of bone marrow was observed, and as a result of observation for 3 months, no abnormality was observed.

A: control

B: 5 μM L-threo-PDMP added

C: 20 μM L-threo-PDMP added

D: 40 μM L-threo-PDMP added

Figure 3:
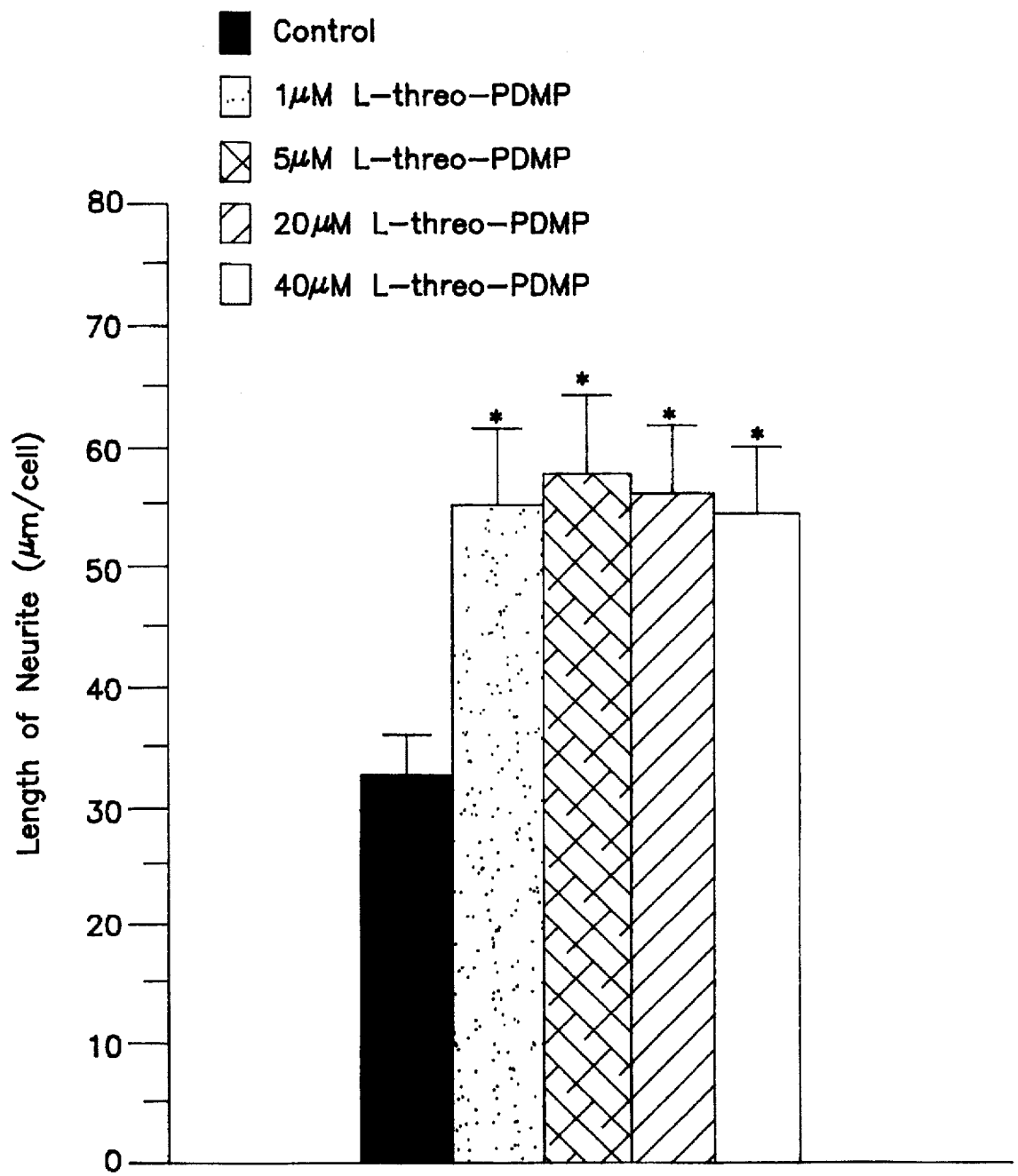

FIG. 3 is a graph showing an accelerating effect of L-threo-PDMP on neurite extension of primary cultured rat cerebral neurocytes.

Figure 4:
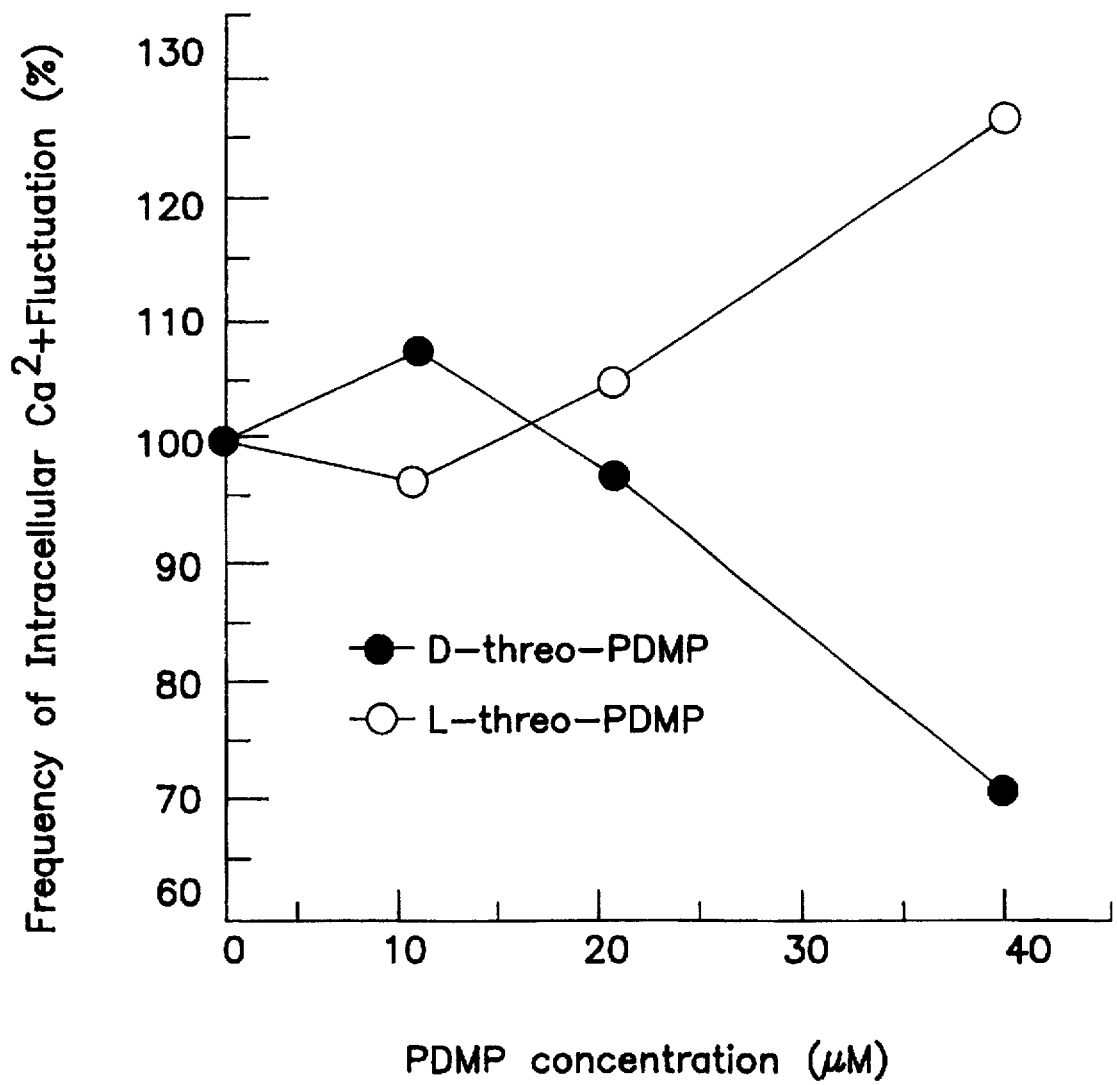

FIG. 4 is a graph showing influences of L-threo-PDMP and D-threo PDMP on frequency (%) of fluctuation of intracellular $Ca^{2+}$, reflecting the number of synapse formation of primary cultured rat cerebral neurocytes.

(BEST MODE FOR PRACTICING THE INVENTION)

In the following, Examples of the present invention are shown, but the present invention is not limited thereby. All of D-threo-PDMP or L-threo PDMP used the following Examples are hydrochlorides, but the same results can be also obtained when other pharmaceutically acceptable salts are used.

EXAMPLE 1

Rat fetuses at the 18th day of pregnancy were taken out, and forebrain base portions of the fetuses were extracted aseptically and cut into small pieces by scissors. After the pieces were treated with papain (in a phosphate buffer containing 0.02% L-cysteine containing 180U papain, 0.02% bovine serum albumin and 0.5% glucose, pH 7.4, at 37° C. for 30 minutes), they were washed with a mixed solution (DF medium) of 1:1 of a Dulbecco modified Eagle's medium and a Ham's F12 medium and suspended in a DF medium containing 5% bovine fetal serum and 5% equine serum. This neurocyte suspension was charged into a culture plate with 24 wells (Falcon, Primaria) in an amount of $1\times10^6$ cells/well. Subsequently, 20 μM D-threo-PDMP or L-threo-PDMP was added, and the primary culture of the neurocytes was carried out for 3 days. After completion of the culture, the cells in the respective wells were washed with a phosphate buffer and recovered by rubber policeman. Further, a ganglioside fraction was extracted by adding chloroform/methanol/water (1:2:0.8) and shaking the mixture for 5 minutes. This ganglioside fraction was dissolved in 50 μl of water, and the amount of ganglioside-binding sialic acid was measured by the method of Hara et al. (Anal. Biochem. 179, 162–166, 1989) to determine a gangliaside content. The no addition group (control) which was defined as 100% was compared with the test groups, and the results are shown in Table 1.

TABLE 1

Influences of D-threo-PDMP and L-threo-PDMP on ganglioside content of primary cultured rat cerebral neurocytes

|  | Ganglioside content |
| --- | --- |
| Control | 100% |
| D-threo-PDMP | 63.4% |
| L-threo-PDMP | 127.1% |

In the treatment with 20 μM D-threo-PDMP, as expected, decrease in the ganglioside level based on inhibition of the glucosylceramide biosynthesizing enzyme was clearly observed. On the other hand, in the neurocytes treated with 20 μM L-threo-PDMP for 3 days, the ganglioside level was increased by about 30% as compared with that of the control. Thus, it was found that L-threo-PDMP has a GSL biosynthesis-accelerating effect on rat cerebral neurocytes and elevates a level of endogenous ganglioside.

EXAMPLE 2

Figure 1:
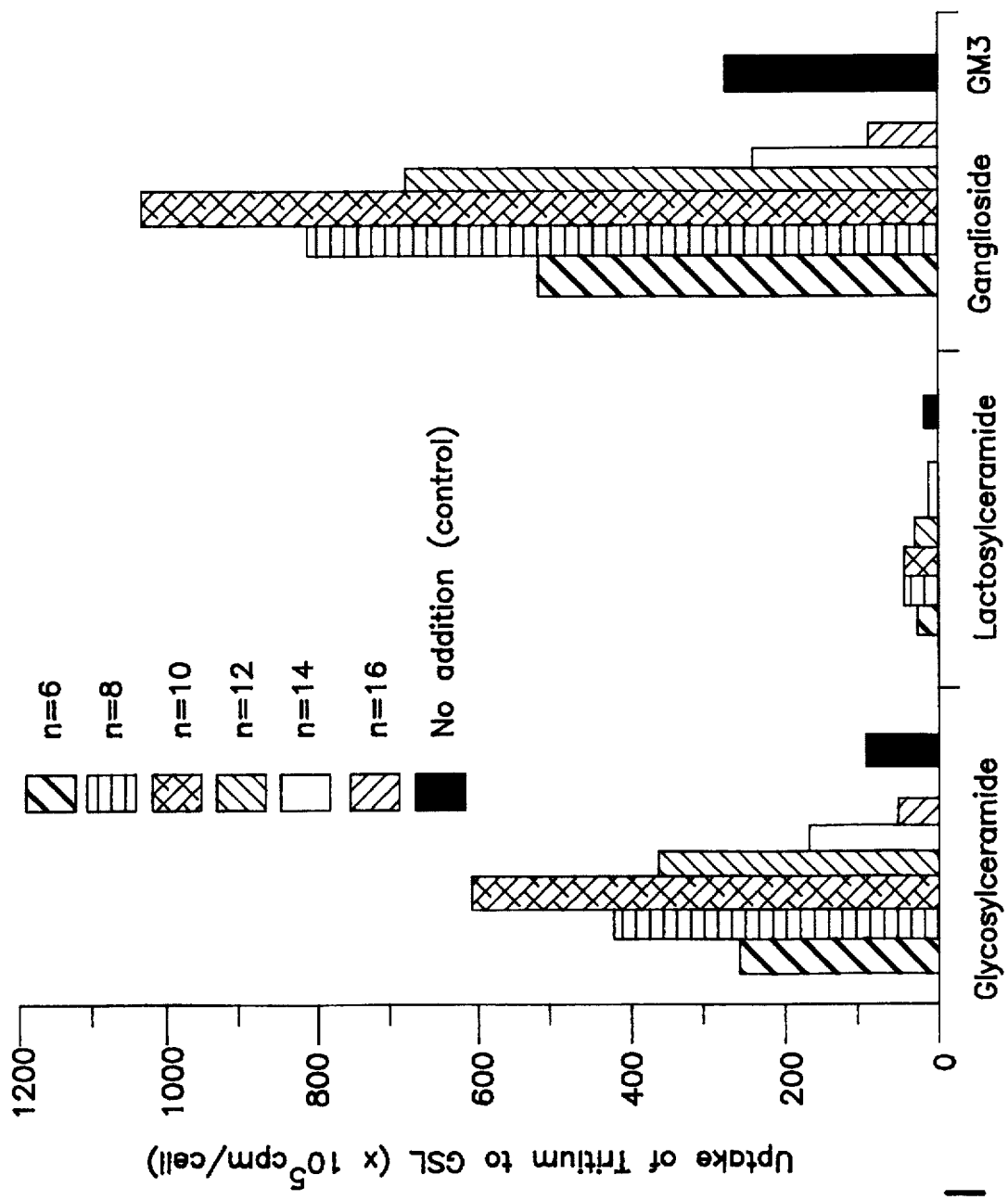
FIG. 1 is a graph showing glycolipid biosynthesis-accelerating actions of L-threo-PDMP and analogues thereof having different acyl chain lengths.
Figure 2A:
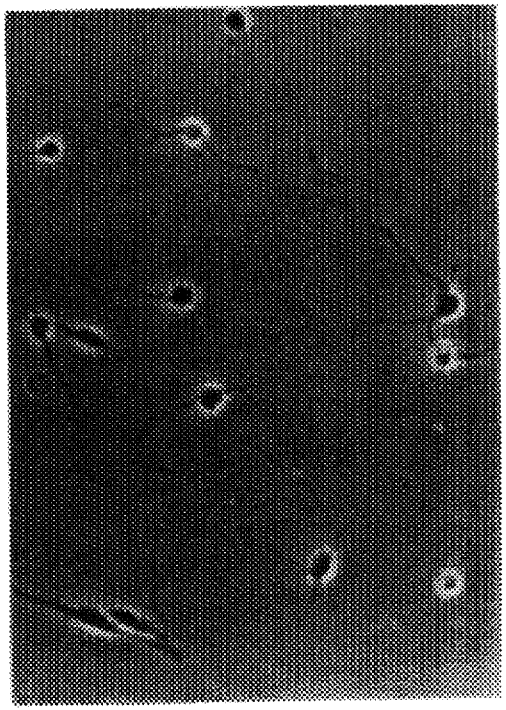
FIGS. 2a–2d are phase contrast microphotographs of biological morphologies showing a neurite extension-accelerating effect of L-threo-PDMP on primary cultured rat cerebral neurocytes (solid lines in the photographs show scales of the cells, and the total length shows 100 nm).
Figure 2B:
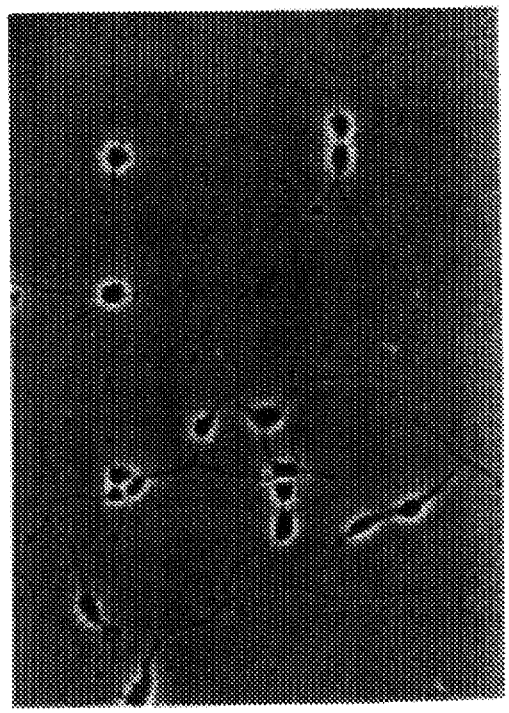
Figure 2C:
Figure 2D:
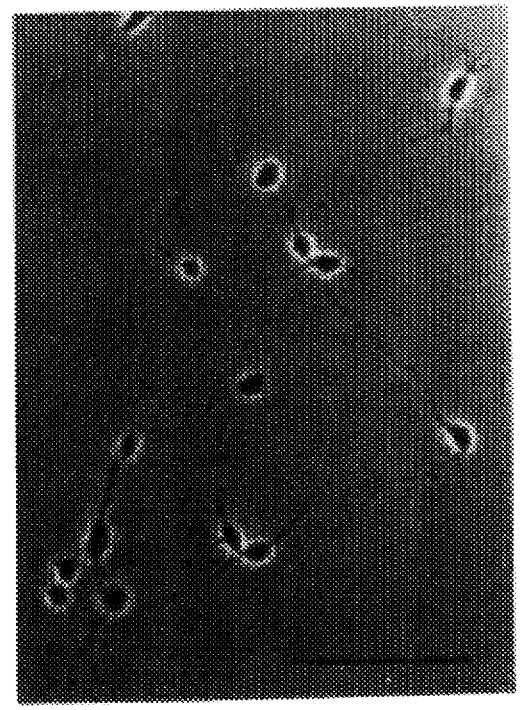

B16 melanoma cells derived from neuroectoderm were charged into a culture plate with 12 wells in an amount of $1\times10^5$ cells/well and cultured for 24 hours in a Dulbecco modified Eagle's medium containing 10% bovine fetal serum. Thereafter, the medium was exchanged with the same culture solution containing 5 μM L-threo-PDMP or analogues thereof in which acyl chain lengths are changed, and $^3$H-galactose was added. After 24 hours, the medium was removed, the cells were washed with 1 ml of a phosphate buffer containing 0.1% EDTA, 1 ml of 0.25% trypsin was added, and the mixture was left to stand at 37° C. for 5 minutes. When the cells were recovered, non-labeled B16 melanoma cells ($1.4\times10^7$ cells) were added, the mixture was washed with a phosphate buffer, and then a mass of the cells was obtained. 4 ml of methanol and chloroform were added successively to the mass of the cells to extract all GSL, followed by evaporation to dryness. The residue was subjected to alkali hydrolysis with chloroform: methanol (1:1) containing 0.2N sodium hydroxide, neutralized with acetic acid and then evaporated to dryness. The product evaporated to dryness was dissolved in water and then desalted with a Sep-Pak cartridge C18 (Waters). The adsorbed GSL was dissolved out by 1 ml of methanol and 4 ml of chloroform-:methanol (1:1) and then evaporated to dryness under a nitrogen stream. Next, the GSL was purified by a conventional method using acetylation by pyridine-acetic anhydride, Florisil column and deacetylation (J. Lipid Res., 12, 257–259, 1971), then desalted and evaporated to dryness. This purified GSL fraction was dissolved in 50 μl of chloroform: methanol (1:1), and 40 μl of the solution was applied to silica gel plate (TLC) and developed with chloroform: methanol:$H_2O$ (60:35:8). Thereafter, the positions of glucosylceramide, lactosylceramide and ganglioside GM3 were confirmed by iodine coloration, they were scratched off from TLC, respectively, and radioactivities thereof were measured by a liquid scintillation counter. The results are shown in FIG. 1. As can be clearly seen from FIG. 1, it was found that among L-threo-PDMP and the analogues thereof in which acyl chain lengths are changed, the compounds of the formula (I) in which n is 6, 8, 10 and 12 significantly accelerate biosynthesis of ganglioside.

EXAMPLE 3

Hippocampi of rat brains at the 0th day after birth were extracted aseptically, subjected to enzyme treatment with papain in the same manner as in Example 1 and then washed with a DF medium. Neurocytes were sowed in a plate with 96 wells which had been covered with poly-L-lysine, at a density of $2\times10^4$ cells/cm$^2$, and at the same time, 5 μM, 20 μM and 40 μM L-threo-PDMP were added, respectively. After culture for 24 hours, the neurocytes were fixed by paraformaldehyde, and a degree of neurite extension was recorded by microphotographs and then observed. As can be clearly seen from the microphotographs of FIG. 2, L-threo-PDMP exhibits a significant neurite-extending action in the primary culture of the rat cerebral neurocytes.

Further, as shown in FIG. 3, when the lengths of the neurites were measured by using four photographs of the respective test groups and statistical processing was conducted, it was apparent that L-threo-PDMP accelerates neurite extension with a significant different of $P<0.005$ over a wide concentration range (1 to 40 μM).

Thus, from Examples 1 to 3, it was strongly suggested that L-threo-PDMP of the present invention and the analogues thereof in which acyl chain lengths are changed have remarkable neurite extension-accelerating actions, i.e., differentiation-accelerating actions to neurocytes by an action of increasing an endogenous ganglioside level of the neurocytes.

EXAMPLE 4

(1) The present inventors have recently advocated a "tracing circuit" model that a dynamic change of synapse binding occurs even in human mature brain, and selective removal of synapse outside a circuit and increase in the number of synapse binding of synapse within the circuit are a mechanism of human long-term memory (Kuroda Y., Neurochem. Intern., 14, 309–319, 1989).

Further, as a method of measuring synapse formation relatively simply and easily, there has been developed a multipoint observation system of $Ca^{2+}$ in neurocytes using Fura-2, and it has been confirmed that the number of synapse formation is in direct proportion to frequency of intracellular $Ca^{2+}$ fluctuation in synchronization therewith (Br. J. Pharmacol., 89, 191–198, 1986; Neurosci. Lett., 78, 69–74, 1987). We investigated influences of L-threo-PDMP and D-threo-PDMP exerted on synapse formation between rat cerebral cortex neurocytes by using this method, and the results are shown below.

Neurocytes of cerebral cortexes of rat fetuses at the 18th to 19th day of pregnancy were isolated by enzyme treatment with papain and cultured in the same manner as in Example 1. By adding L-threo-PDMP or D-threo-PDMP and measuring frequency of intracellular $Ca^{2+}$ fluctuation from the first day of the culture, a degree of synapse formation was examined. The results are shown in FIG. 4, and increase in the number of synapse formation depending on a dose by L-threo-PDMP was clearly observed. Thus, L-threo-PDMP not only has an action of accelerating extension of neurites, but also accelerates formation of synapse so that possibility of being effective for curing various neuronal diseases was strongly suggested. Further, D-threo-PDMP having a GSL biosynthesis-inhibiting action suppressedly acted on synapse formation so that it was found that endogenous GSL, particularly ganglioside fulfills an important function in the process of synapse formation.

(2) By using cerebral cortexes of rat fetuses at the 16th day of pregnancy similarly as in (1), explant culture was carried out by the following method to confirm the effect of the agent for curing neuronal diseases of the present invention.

That is, according to the method described in J. Neurochem., 61, 2155–2163 (1993), the above cerebral cortexes were cut into small pieces, and when culture of tissues including cerebral cortex neurons was conducted by culturing the pieces in a medium containing no serum, as groups to which the medicine was administered, L-threo-PDMP or D-threo-PDMP was added to the medium so that the concentration became 5 to 20 μM, and the mixtures were cultured for 2 days. The effect of neurite extention by administering the medicine after the culture was judged by measuring the number of neurocytes having neurites existing in the explants (the cultured tissues).

As a result, the number of the above neurocytes in the group to which 10 μM L-threo-PDMP was administered was about one and half times of that of the group to which no medicine was administered. On the other hand, in the group to which 10 μM D-threo-PDMP was administered, the neurite extension-accelerating effect observed in the case of L-threo-PDMP was not observed.

As described above, even in the tissue culture of cerebral cortexes, effectiveness of L-threo-PDMP to neurite extension was exhibited so that it was strongly suggested that by exhibiting the similar action in vivo when the agent for curing neuronal diseases of the present invention was administered to mammals including human, it is effective for curing neuronal diseases accompanied with a regressive change of cerebral cortex neurons such as Alzheimer's disease, etc.

EXAMPLE 5

Preparation Example of Capsule 100 mg of L-threo-PDMP hydrochloride, 150 mg of potato starch, 50 mg of light silicic acid anhydride, 10 mg of magnesium stearate and 765 mg of lactose were mixed uniformly and 200 mg of this mixture was apportioned and charged into a hard capsule.

Preparation Example of Tablet 100 mg of L-threo-PDMP hydrochloride, 670 mg of lactose, 150 mg of potato starch, 60 mg of crystalline cellulose and 50 mg of light silicic acid anhydride were mixed and to the mixture was added a solution of 30 mg of hydroxypropyl cellulose dissolved in methanol (10% by weight of hydroxypropyl cellulose). The mixture was kneaded and then granulated. Next, the granules were extruded through a screen with a size of 0.8 mm to obtain fine granules. After the granules were dried, 15 mg of magnesium stearate was added thereto and each 200 mg of the mixture was tableted.

Preparation Example of Injection

Propylene glycol was added to 100 mg of L-threo-PDMP hydrochloride so that the total amount was 10 ml to dissolve L-threo-PDMP hydrochloride. After this solution was sterilized and filtered, each 0.2 ml was apportioned to ampoules and the ampoules were sealed.

In the respective preparation examples, 100 mg of L-erythro-PDMP hydrochloride was used in place of L-threo-PDMP hydrochloride to obtain the respective preparations of capsules, tablets and injections.

EXAMPLE 6

Liposome Preparation and Kinetics in Vivo

As shown in Examples 3 and 4, L-threo-PDMP exhibits an action to central nervous system tissues (cerebral cortex and around hippocampus of brain) so that it is required that it permeates a blood-brain barrier and elevates a concentration in brain by intravenous administration. L-threo-PDMP is a fat-soluble substance, and its solubility in physiological saline is maximally 0.5 mg/ml so that when it is solubilized by using a surfactant in order to enable intravenous administration, it is taken into reticuloendothelial tissues before reaching a target organ, whereby it cannot be expected to obtain an effective pharmaceutically effective concentration at an action site.

In view of the above situations, the present inventors have studied a method of elevating transition from blood to central nervous tissues (particularly cerebral cortex and around hippocampus of brain) and consequently found that the above problem can be solved by incorporating L-threo-PDMP into nanosphere liposome as shown in the following experiment.

That is, they have found that by incorporating L-threo-PDMP into nanosphere liposome and intravenously administering the mixture to rats, an effective concentration for exhibiting a pharmaceutical effect in brain can be maintained.

11

(1) Preparation of liposome preparation

A chloroform solution containing phosphatidylcholine (18 μmol), phosphatidylserine (3 μmol) and cholesterol (9 μmol) and a chloroform:methanol (2:1) solution of [$^{14}$C]-L-threo-PDMP (0.5 mg, 5.5 μCi) were mixed, and the mixture was condensed and evaporated to dryness in a flask under a nitrogen stream. 1 ml of physiological saline was added thereto, and the mixture was stirred, subjected to ultrasonic treatment for 10 minutes and then passed through a membrane filter (CORNING Disposable Sterile Syringe Filter, 25 mm, 0.2 μ, Cellulose Acetate Membrane) to prepare a nanosphere liposome liquid containing L-threo-PDMP. The method itself of preparing the nanosphere liposome is a known method (see Japan Medicine Society, the 114th Annual Meeting, Summaries of Lectures 4, p. 32, Subject No. 13–127 (1994)).

(2) Kinetics in vivo

The liposome solution (4.54 μCi) of [$^{14}$C]-L-threo-PDMP prepared in the method of the above (1) and a physiological saline solution (4.54 μCi) of 0.5 mg/ml of [$^{14}$C]-L-threo-PDMP were intravenously administered to Wister strain male rats (10 weeds old) from femoral arteries over 30 seconds, respectively, and blood was collected with a lapse of time. From blood samples, L-threo-PDMP was quantitated according to a conventional method (J. Lipid. Res., vol. 32, 713–722, 1991). As a result of examining a change of a concentration in blood with a lapse of time, the results which could be analyzed by a typical 2-compartment model were obtained. By a simplex method of non-linear least square method program MULTI, pharmaceutically kinetic parameters were calculated. As a result, the half-times of disappear were 2.56 minutes (liposome) and 2.77 minutes (physiological saline) in the first phase and 25.2 minutes (liposome) and 27.5 minutes (physiological saline) in the second phase.

From the above results, it was observed that the area under the concentration time curve of the medicine in blood (AUC; area under the concentration curve) is increased by slightly less than 9 times by preparation of liposome, and the residual property of L-threo-PDMP in blood is elevated by preparation of liposome. As a result of determining, by simulation, a time when the peripheral compartment concentration of the 2-compartment model was maximum, it was 10 minutes so that it was estimated that the concentration in brain is also maximized in 10 minutes. Therefore, the concentration in brain and the concentration in blood were measured at 10 minutes and 60 minutes when an equilibrium state of the compartment was established. Also the concentration in brain, L-threo-PDMP was quantitated according to a conventional method (J. Lipid. Res., vol. 32, 713–722, 1991). The results are shown in Table 2.

12

TABLE 2

Concentration in blood and concentration in brain after intravenously administering L-threo-PDMP to rats

|  | Liposome | | Physiological saline solution | |
|---|---|---|---|---|
|  | 10 min | 60 min | 10 min | 60 min |
| Concentration in blood (pmol/ml) | 1789.1 | 170.5 | 451.2 | 118.0 |
| Concentration in brain (μM) | 25.7 | 1.0 | 2.5 | ND |
| Brain/blood concentration ratio | 0.0144 | 0.0060 | 0.0056 | ND |

From the results of Table 2, it became apparent that by preparation of liposome, the concentration in brain is also elevated by about 10 times as compared with administration of the physiological saline solution.

As a result of carrying out simulation of a continuous intravenous injection (intravenous injection) of a peripheral compartment by using the ratio of concentration in brain/concentration in blood in a steady state (60 minutes) of liposome administration, it became apparent that it is possible to reach within a 1% limit of the concentration in brain in a steady state by the continuous intravenous injection for 4 hours.

From an in vitro experiment, an pharmaceutical effect has been observed by culture at 25 μM for 24 hours in B16 melanoma cells derived from neuroectoderm, culture at 40 μM for 8 hours in culture of neurocytes of cerebral cortexes of rat fetuses and in the range of 5 to 20 μM in culture of cerebral cortex pieces of rat fetuses. By applying these conditions to an in vivo experiment, simulation was carried out. The results obtained by calculating, by simulation, a rate and a liquid amount of continuous intravenous injection required for reaching a predetermined steady concentration in brain are shown in Table 3.

TABLE 3

Rate and liquid amount of continuous intravenous injection for reaching a steady concentration in brain

| Concentration in brain in steady state (μM) | Rate of continuous intravenous injection of liposome (pmol/h) | (ml/h) | Liquid amount of liposome (ml) | | Rate of continuous intravenous injection of physioogical saline solution (pmol/h) | (ml/h) | Liquid amount of physiological saline solution (ml) | |
|---|---|---|---|---|---|---|---|---|
|  |  |  | 4 hours* | 28 hours |  |  | 4 hours** | 28 hours |
| 50 | 177620.0 | 0.152 | 0.608 | 4.256 | 1672200.0 | 1.427 | 5.708 | 39.956 |
| 25 | 88810.0 | 0.076 | 0.304 | 2.128 | 836100.0 | 0.713 | 2.852 | 19.964 |
| 10 | 35524.0 | 0.030 | 0.120 | 0.840 | 334440.0 | 0.285 | 1.142 | 7.980 |
| 5 | 17762.0 | 0.015 | 0.060 | 0.420 | 167220.0 | 0.143 | 0.572 | 4.004 |

*, **: reaching within 1% of the concentration in brain in a steady state in 4 hours From the results of the above simulation, in the physiological saline solution, it is 39.956 ml/28 hrs in the case of the steady concentration in brain being 50 μM and 19.964 ml/28 hrs in the case of 25 μM so that it can be seen that the liquid amount of continuous intravenous injection is too large relative to the total rat humor amount. On the other hand, in the liposome solution, it is 4.256 ml/28 hrs in the case of the steady concentration in brain being 50 μM and 2.128 ml/28 hrs in the case of 25 μM so that it can be said that this liquid amount is a liquid amount within a physiological range to be administrated.

From the above results, it is apparent that by converting L-threo-PDMP into liposome, an effective pharmaceutical effect is exhibited even to mammals including human by intravenously injecting a suitable liquid amount continuously.

(UTILIZABILITY IN INDUSTRY)

The agent for curing neuronal diseases of the present invention accelerates neurite extension and synapse formation by elevating biosynthesis of endogenous GSLs of neurocytes, particularly ganglioside, whereby it is effective for curing various diseases of central nervous system and peripheral nervous system. It is effective for various central nervous system diseases which are expected to be cured by regenerating nerve fibers, for example, cerebral apoplexy, cerebral infarction, cerebral hemorrhage, cerebral injury, dysmnesia, senile dementia, Alzheimer's disease, parkinsonism, etc. Also, it is effective for various peripheral nervous system diseases, for example, polyneuropathy caused by cacochymia, mechanical neuropathy, toxic neuropathy, etc.

The agent for curing neuronal diseases of the present invention can pass a blood-brain barrier (J. Lipid Res., 32, 713–722 (1991)) so that it is effective for cerebral neuronal diseases as an injection or an oral agent. In particular, nanosphere liposome (lipid nanosphere) on which the agent for curing neuronal diseases of the present invention is carried can not only heighten a concentration in blood without being taken into reticuloendothelial tissues and lower a minimum effective dose required for exhibiting a pharmaceutical effect, but also pass a blood-brain barrier by about 10 times as compared with a physiological saline solution so that it is extremely effective when the agent for curing neuronal diseases of the present invention is used for curing cerebral neuronal diseases.

We claim:

1. A liposome preparation composition for treating neuronal diseases treatable by elevating biosynthesis of endogenous glycosphingolipids (GSLs) of neurocytes comprising at least one 2-acylaminopropanol derivative of the formula

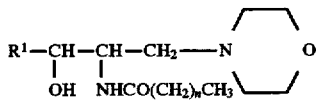

wherein $R^1$ is phenyl or cyclohexyl, each of which may be substituted by 1 to 3 members selected from the group consisting of alkyl, alkoxy, hydroxy and nitro, or $R^1$ is alkyl and n is an integer of 0 to 16 and said derivative has efficacy for accelerating biosynthesis of glycosphingolipids, accelerating neurite extension and/or accelerating synapse formation, or a pharmaceutically acceptable salt thereof and a phospholipid.

2. The liposome preparation composition according to claim 1, wherein n of the formula (I) is 6 to 16.

3. The liposome preparation composition according to claim 1, wherein $R^1$ of the formula (I) is phenyl.

4. The liposome preparation composition according to claim 1, wherein the 2-acylaminopropanol derivative represented by the formula (I) is a L-threo isomer.

5. The liposome preparation composition according to claim 4, wherein the 2-acylaminopropanol derivative is a L-threo isomer of 1-phenyl-2-decanoylamino-3-morpholino-1-propanol, or a salt thereof.

6. The liposome preparation composition according to claim 1 wherein the liposome is capable of maintaining an effective concentration for exhibiting a pharmaceutical effect in brain when intravenously administered.

7. The liposome preparation composition according to claim 1 wherein the liposome is a nanosphere liposome.

8. A method of treating neuronal diseases treatable by elevating biosynthesis of endogenous glycosphingolipids (GLSs) of neurocytes in warm-blooded animals comprising administering to warm-blooded animals an amount of a liposome composition comprising at least one 2-acylaminopropanol derivative of the formula

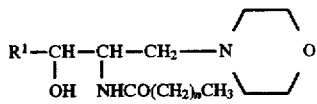

wherein $R^1$ is phenyl or cyclohexyl, each of which may be substituted by 1 to 3 members selected from the group consisting of alkyl, alkoxy, hydroxy and nitro, or $R^1$ is alkyl and n is an integer of 0 to 16 and said derivative has efficacy for accelerating biosynthesis of glycospyhingolipids, accelerating neurite extension and/or accelerating synapse formation, or a pharmaceutically acceptable salt thereof and a phospholipid sufficient to treat said neuronal diseases.

9. The method of claim 8 wherein the compound of Formula I is a L-threo isomer.

10. The method of claim 8 wherein the compound of Formula I is the L-threo isomer of 1-phenyl-2-decanoylamino-3-morpholino-1-propanol or a non-toxic, pharmaceutical acceptable acid addition salt thereof.

* * * * *

UNITED STATES PATENT AND TRADEMARK OFFICE
CERTIFICATE OF CORRECTION

PATENT NO. : 5,707,649
DATED      : January 13, 1998
INVENTOR(S) : INOKUCHI et al It is certified that error appears in the above-identified patent and that said Letters Patent is hereby corrected as shown below: On the title page:

Item [75]:   please correct the inventor's name to read

--JIN-ICHI--

Signed and Sealed this

Twenty-fourth Day of March, 1998

Attest:

BRUCE LEHMAN

Attesting Officer    Commissioner of Patents and Trademarks